United States Patent
Ukis et al.

(10) Patent No.: US 10,684,919 B2
(45) Date of Patent: Jun. 16, 2020

(54) QUERY WITH DATA DISTRIBUTION IN A HOSPITAL NETWORK

(71) Applicants: Vladyslav Ukis, Nürnberg (DE); Lutz Dominick, Eggolsheim (DE)

(72) Inventors: Vladyslav Ukis, Nürnberg (DE); Lutz Dominick, Eggolsheim (DE)

(73) Assignee: Siemens Healthcare GmbH, Erlangen (DE)

( * ) Notice: Subject to any disclaimer, the term of this patent is extended or adjusted under 35 U.S.C. 154(b) by 494 days.

(21) Appl. No.: 15/333,524

(22) Filed: Oct. 25, 2016

(65) Prior Publication Data
US 2018/0113765 A1 Apr. 26, 2018

(51) Int. Cl.
| | |
|---|---|
| G06F 7/00 | (2006.01) |
| G06F 17/00 | (2019.01) |
| G06F 11/14 | (2006.01) |
| G06F 16/51 | (2019.01) |
| G06F 16/25 | (2019.01) |
| G06F 16/23 | (2019.01) |
| G16H 40/20 | (2018.01) |
| G06F 19/00 | (2018.01) |

(52) U.S. Cl.
CPC ...... *G06F 11/1451* (2013.01); *G06F 11/1464* (2013.01); *G06F 16/2358* (2019.01); *G06F 16/252* (2019.01); *G06F 16/51* (2019.01); *G06F 19/321* (2013.01); *G16H 40/20* (2018.01); *G06F 2201/80* (2013.01); *G06F 2201/84* (2013.01)

(58) Field of Classification Search
None
See application file for complete search history.

(56) References Cited

U.S. PATENT DOCUMENTS

| | | | |
|---|---|---|---|
| 6,915,266 B1 | 7/2005 | Saeed et al. | |
| 8,606,594 B2 | 12/2013 | Stern et al. | |
| 8,875,097 B2 | 10/2014 | Dasch et al. | |
| 9,009,075 B2 | 4/2015 | Dominick et al. | |
| 9,398,079 B2 | 7/2016 | Dominick et al. | |
| 2007/0011024 A1 | 1/2007 | Dale et al. | |
| 2009/0193394 A1* | 7/2009 | Dasch | G06F 9/4488 717/120 |
| 2013/0054272 A1* | 2/2013 | Rangadass | G16H 10/60 705/3 |
| 2015/0244687 A1* | 8/2015 | Perez | H04L 63/0428 726/4 |
| 2016/0004820 A1* | 1/2016 | Moore | H04W 4/21 705/3 |
| 2016/0210427 A1* | 7/2016 | Mynhier | G16H 50/20 |

OTHER PUBLICATIONS

European Search Report for corresponding Application No. 17195922. 4-1126, dated Mar. 22, 2018.

* cited by examiner

*Primary Examiner* — Tuan A Pham
(74) *Attorney, Agent, or Firm* — Lempia Summerfield Katz LLC

(57) ABSTRACT

A system and method for negotiating between a business intelligence application and one or more data sources. Business data from devices is received, identified and stored using a data meta model that is updated as devices and the hospital environment change. The data meta model allows the business intelligence application to negotiate with the hospital data sources to access relevant data for evaluations. The data meta model includes an object model that is configurable, updatable, adaptable, and evolvable over time.

8 Claims, 6 Drawing Sheets

QUERY WITH DATA DISTRIBUTION IN A HOSPITAL NETWORK

TECHNICAL FIELD

The present embodiments relate to integrating business intelligence applications into a hospital network.

BACKGROUND

Hospitals, diagnostic centers and medical imaging centers may use multiple types of equipment. A diverse collection of imaging or scanning devices may be used to provide services to patients and/or assist in diagnosis. A single hospital may, for example, provide x-ray examinations, computed tomography (CT) imaging, ultrasound, magnetic resonance imaging (MRI), positron emission tomography (PET) imaging, and interventional radiology among other procedures or imaging techniques. Each procedure may involve one or multiple machines, one or more imaging devices, and one or more workflows.

In order to gain insights in to how well a hospital is running its business, performing procedures, or operating its devices, business intelligence applications may be used to evaluate clinical workflows and the hospital environment. The challenge for business intelligence applications is to identify data that is relevant to the analysis. The complexity of a hospital environment, including the multiple types of devices and data, constant changes in the data and layout, variance in data storage location, and relationships between the data and the hospital, makes the identification of relevant data difficult. Business intelligence applications may be unable to negotiate with data sources in the hospital to acquire relevant data. Furthermore, even when connections from business intelligence applications to relevant data have been previously established, updates of the relevant aspects (organizational structures, device specifics, medical considerations and planning details) may hamper the ability of the applications to access relevant data.

BRIEF SUMMARY

Embodiments are provided that allow a business intelligence application to access relevant data. Business data from devices is received, identified and stored using a data meta model that is updated as devices and the hospital environment change. The data meta model allows the business intelligence application to negotiate with the hospital data sources to access relevant data for evaluations. The data meta model includes an object model that is configurable, updatable, adaptable, and evolvable over time. The data meta model is called by the business intelligence applications in order to handle variance and/or diversity in memory locations, data formats, and/or data source differences.

In one aspect, a system for integrating one or more business intelligence applications into a hospital network is provided. The system comprises one or more medical devices, an object oriented data repository, a user interface, and a data meta processor. The one or more medical devices in a hospital are configured to generate data. The data repository is configured to store the data. The user interface is configured to execute the one or more business intelligence applications using the data. The data meta processor is configured to receive the data from the one or more medical devices, identify attributes of the data, and to store the data in the data repository with an object identifier generated based on attributes of the data, a fleet map of the one or more medical devices, and a site map of the hospital network. The user interface is configured to retrieve the data from the data repository using the object identifier.

In a second aspect, a method is provided for integrating one or more business intelligence applications into a hospital network. Business data is generated by a plurality of medical devices. A plurality of data sources and a plurality of data attributes are identified for the business data. A data meta model is generated. The data meta model includes a plurality of object identifiers that describe what the business data contains and where the business data is stored. A request is received from a business intelligence application. The object identifier for data is provided by the data meta model.

In a third aspect, a method is provided for updating a data meta model. Business data relating to a medical device is received. An object in the data meta model that is related to the business data is identified. One or more updates to the business data are identified. The object is updated with the one or more updates. One or more data paths for one or more business intelligence applications are updated.

The present invention is defined by the following claims, and nothing in this section should be taken as a limitation on those claims. Further aspects and advantages of the invention are discussed below in conjunction with the preferred embodiments and may be later claimed independently or in combination.

BRIEF DESCRIPTION OF THE DRAWINGS

The components and the figures are not necessarily to scale; emphasis instead being placed upon illustrating the principles of the invention. Moreover, in the figures, like reference numerals designate corresponding parts throughout the different views.

DETAILED DESCRIPTION

Figure 1:
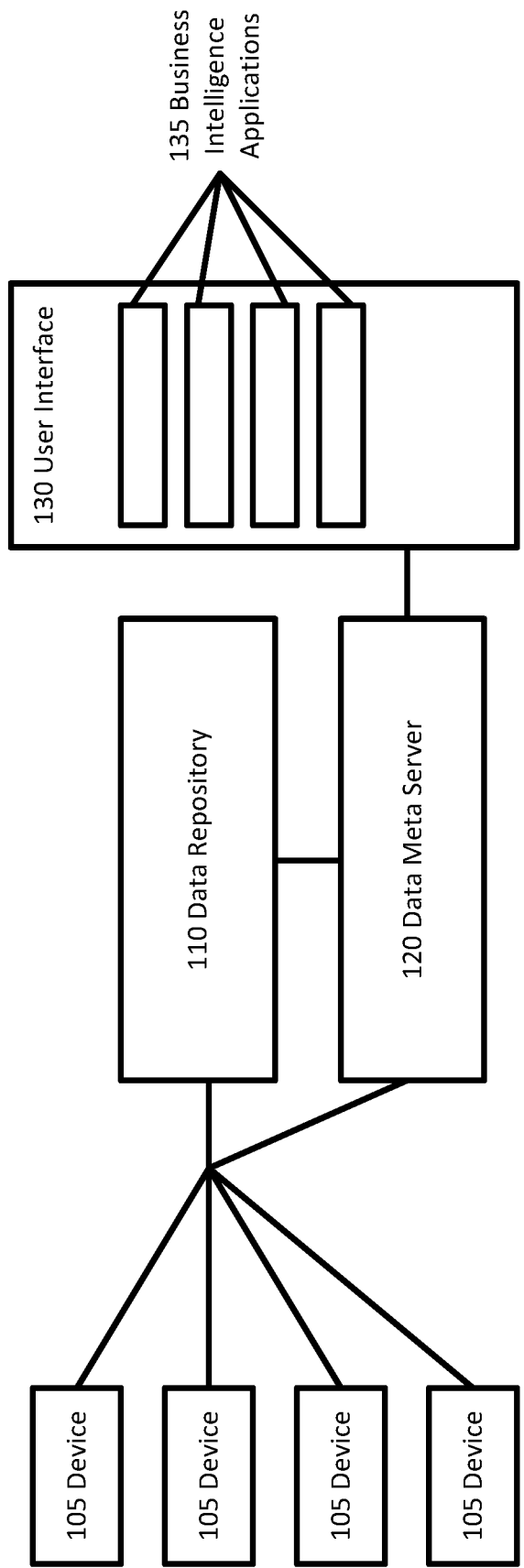
FIG. 1 depicts an example system for integrating business intelligence into a medical environment.

Business intelligence applications may be used to evaluate an operation (e.g., hospital or medical group) by using data from multiple different sources. A hospital, for example, may produce vast amounts of data relating to different procedures in different formats. Business intelligence applications select relevant data from the vast amounts of data to generate analysis of the hospital's operation. To acquire relevant data, the identity of the data is determined. Once the relevant data is identified, the business intelligence applications are connected to or access the relevant data, which may be in many disparate locations.

One example of a business intelligence application is an application that evaluates examination duration and patient changes for CT scanners in a hospital. The analysis derived from the business intelligence application may indicate, for example, that a change in the workflow may produce shorter turnaround time and as such allow the hospital to run more efficiently. To perform the evaluation, the business intelligence application needs data from each of the CT scanners, data relating to the workflow used in the scan, possibly patient data, and/or data relating to the hospital environment (e.g. the staff or personal involved in each scan). The business intelligence application may be of third-party origin, and may not be able to identify the physical and organizational structure at the hospital. For example, the business intelligence application may have been written or designed for a different hospital. Even only considering scan data, there may exist multiple different types or formats of data for different CT scanners, different clinical workflows, different locations in the hospital network, different users, etc. Beyond having different equipment, each different hospital or site (e.g. for a multi-site hospital system) may have different protocols or workflows for each procedure. A business intelligence application crafted by a third party may not be able to access or identify each separate piece of data required to make a proper evaluation. As such, the ability to craft a business intelligence application to run at separate hospitals or sites is prohibitive.

A custom business intelligence application may be created that aligns specifically with the setup at a specific hospital. A custom setup involves additional time for each hospital or site and may not offer comparable evaluations between sites or hospitals. Additionally, even though the application may function properly at first, updates to any relevant aspects of the application (organizational structures, device specifics, medical considerations and planning details) may occur. An initial alignment at development time may not be up-to-date and may not be always effective and not always efficient. As such, the efficacy of the business intelligence application may degrade over time as updates and alterations are made to the hospital network. Each update may require the application be rewritten or reworked. Even a small change in the equipment or protocols may alter the availability of information needed for accurate evaluations. Project specific solutions create constant incompatibility and the need to adapt to unknown change on-site, requiring development teams onsite.

Systems and methods are provided herein that allow a business intelligence application to be efficiently crafted and deployed at a hospital. Relevant data for the business intelligence application is identified and stored using a data meta model that is updated as devices and the hospital environment changes. The data meta model allows the business intelligence application to seamlessly negotiate with the hospital data sources to access relevant data. The data meta model includes an object model that is configurable, updatable, adaptable, and evolvable over time. Fully automated background maintenance of the data meta model is possible by analyzing incoming data from the data sources. The data meta model replaces manual development of code for business intelligence applications by allowing for a run-time execution of evaluations that may be generated with a user interface. The data meta model and user interface are kept automatically up to date by dedicated modules, along with monitoring the changes onsite. The updates use a set of map changes that are automatically detected by the data meta model and the modules that maintain the maps. Updates are supported by a history function for all maps and their entities, to allow a query of the changes. The changes may be traceable.

A user interface may access the data meta model to create a customized, full-fledged business intelligence evaluation report. The user interface allows building evaluations in a guided way, across all or many data sources, with auto re-adaptation to fleet map, site map, and business data map changes, as automated maintenance to the existing evaluations. Third party application integration is automated (e.g., a new function from an external source used to benchmark may be implemented without additional coding). A third-party application that has a preconfigured set of capabilities and/or functions may negotiate with the data meta model allowing both automated integration in the user interface and in the updating process.

The disclosed embodiments may be implemented to optimize a hospital system leading to an improvement in the computational system. The embodiments improve the efficiency and function of business intelligence applications run in or on the hospital network. The increased efficiency and usage of resources may lead to less setup (fewer pieces of equipment), fewer errors, and less maintenance of the business intelligence applications and system.

FIG. 1 depicts a system for integrating business intelligence into a medical environment. The system includes one or more medical devices 105 that generate data. The data may be stored at the medical devices 105 or in a data repository 110. The data repository 110 may be in the cloud or on-site. The system includes one or more user interfaces 130 to evaluate the data stored in the data repository 110. The user interface 130 may be configured to execute business intelligence applications 135. The user interface 130 may be configured to craft a business intelligence application 135. The system further includes a data meta model server 120 (DM server). The one or more medical devices 105 may be connected to the DM server 120. A user interface 130 may access the data from the one or more medical devices 105 stored in the data repository 110 or on the medical devices 105 though the DM server 120. The DM server 120 may be configured to facilitate communications between business intelligence applications running on the user interface 130 and data sources, e.g. the one or more medical devices 105. Additional, different or fewer components may be included. For example, the system may include a computer network to facilitate communication. The system may include additional servers or devices, such as a server for tracking personal at a hospital. One or more of the components may be located on-site or in the cloud.

The medical devices 105 may be different modalities, such as an ultrasound scanner, a CT scanner, and an MRI scanner. In other embodiments, two or more of the medical devices 105 are of a same modality, such as two x-ray scanners. The medical devices 105 may include or connect with one or more picture and archiving and communications systems (PACS). A PACS is a computing system used to transfer, store, display, and manage medical images and associated administrative data. The PACS may store raw unprocessed data, preprocessed data, or fully processed data. The PACS may be a part of the data repository 110. The data repository might also exist in the form of a Vendor Neutral Archive (VNA).

The medical devices 105 may also be referred to as medical scanning devices, imaging devices or scanning devices. The one or more medical devices 105 may include imaging devices such as magnetic resonance image (MRI) scanners, positron emission tomography (PET) scanners, Single-photon emission computed tomography (SPECT) scanners, ultrasound devices, tomography devices, among others. The medical devices 105 may include any type of imaging device or medical diagnostic device that is connected to a medical or hospital network. Each medical device 105 may be configured to generate data (such as image data) relating to an object (e.g. a patient or a portion of the patient). The medical devices 105 may operate using a formatting standard such as the DICOM standard. DICOM is a standard used for storage and transmission of medical image data including for example, 2D, 3D, and video images. The medical imaging devices 105 may operate using alternative standards such as the Health Level-7 (HL7) standard. Other formats or standards may be used by different devices. All the medical imaging devices 105 use the same format, but a sub-set may use one or more different formats.

The data from the medical device 105 may include both scan results and administrative data (e.g. business data) related to the scan or study. The scan results may include image data or other diagnostic data. Image data is data representing the patient that may be used to generate an image of the patient. The data is formatted for display (e.g., RGB values) or as scalars based on the scanning. Any format may be used for the image data. The medical imaging device 105 may generate one or more two-dimensional images that are subsequently stitched together to create a three-dimensional image or a moving image. The administrative data may include information regarding the scan protocol (e.g. the type of scan, the region of the body, patient information). For example, when using the DICOM standard, the administrative data may include a network message that is initiated by the scanning equipment. The message, referred to as a modality performed procedure step (MPPS), is also sent to the PACS and/or other systems such as a radiology information system (RIS). The message carries information about the settings for the scan that was performed by the medical imaging device 105 during acquisition.

In certain embodiments, the scan data may include additional scan protocol data. The scan data may contain a unique identifier for the scan or the study. The scan data may contain data related to the type of equipment that originally acquired the scan data. The scan data may include data related to the manufacturer, data related to the manufacturer's model name, a description of the study or series of images, an identifier for the acquisition protocol, the target region, the acquisition type, the procedure context, the acquisition parameters (e.g. exposure time, scanning length), the dose, the patient, the physician, etc.

The scan data (image data and business data) may be transmitted and stored locally at the medical device 105, in the data repository 110 or on the DM server 120. In certain embodiments, only the business data (e.g. the attributes, administrative data, and or data describing the scan) is stored in the data repository 110 or on the DM server 120. The location or address where the scan data is stored or located may be determined by the DM server 120. Alternatively, the DM server 120 may assign an identifier or pointer to the location where the scan data is stored (e.g. on a local PACS).

The data repository 110 (database) may be configured to store data received from the one or more medical devices 105. The data repository 110 may be configured to store the data using address based identifiers (e.g. paths) defined by a data meta model. The data repository 110 may store the data using an object based architecture. The data may be managed and addressed as objects that include descriptive properties. The data repository 110 may be located locally onsite at a hospital or in the cloud.

The one or more user interfaces 130 may be configured to run or generate business intelligence applications. The one or more user interfaces 130 may be, for example, a graphical user interface (GUI) that is configured with a command line to allow a user to generate script like evaluations. The one or more user interfaces 130 may be a workstation, home computer, mobile device, server (e.g., website) or may be provided over a network to a user. The one or more user interfaces 130 may communicate with the DM server 120 to access relevant data for the business intelligence applications.

The DM server 120 may include one or more servers, workstations, databases, and other machines connected together. The term DM server 120 is used herein to collectively include the computational, interface API's and business intelligence capabilities residing in both local and cloud based systems including the systems used for creating, maintaining, accessing, and updating the data meta model. The user interface 130 may be a part of the DM server 120 or may be separate component that communicates with the DM server 120 over the network. The DM server 120 may be connected to the one or more medical devices 105. The DM server 120 may receive scan data and/or administrative data from the medical devices 105 or other data sources. The DM server 120 may be configured to facilitate or run business intelligence applications.

The DM server 120 may be configured for automated run-time configurable data relevance detection with automated suggestion, automated integration of applications and data, evolvable object maps with automated update detection and unattended reification of impacted business intelligence application coding. The DM server 120 may be configured to identify a type of data received from the medical devices 105 and generate or update an identifier for storing and accessing the data. The DM server 120 may be configured to identify one or more requested inputs from a business intelligence application and match the input to a data path (identifier of the location of the data in memory). The DM server 120 may be configured for updating the mapping as changes occur to either the medical devices 105 (data sources) or business intelligence applications. The DM server 120 may be configured to provide a data meta model of available data sources and links to a user interface 130 for a quick report generation capability.

Figure 2:
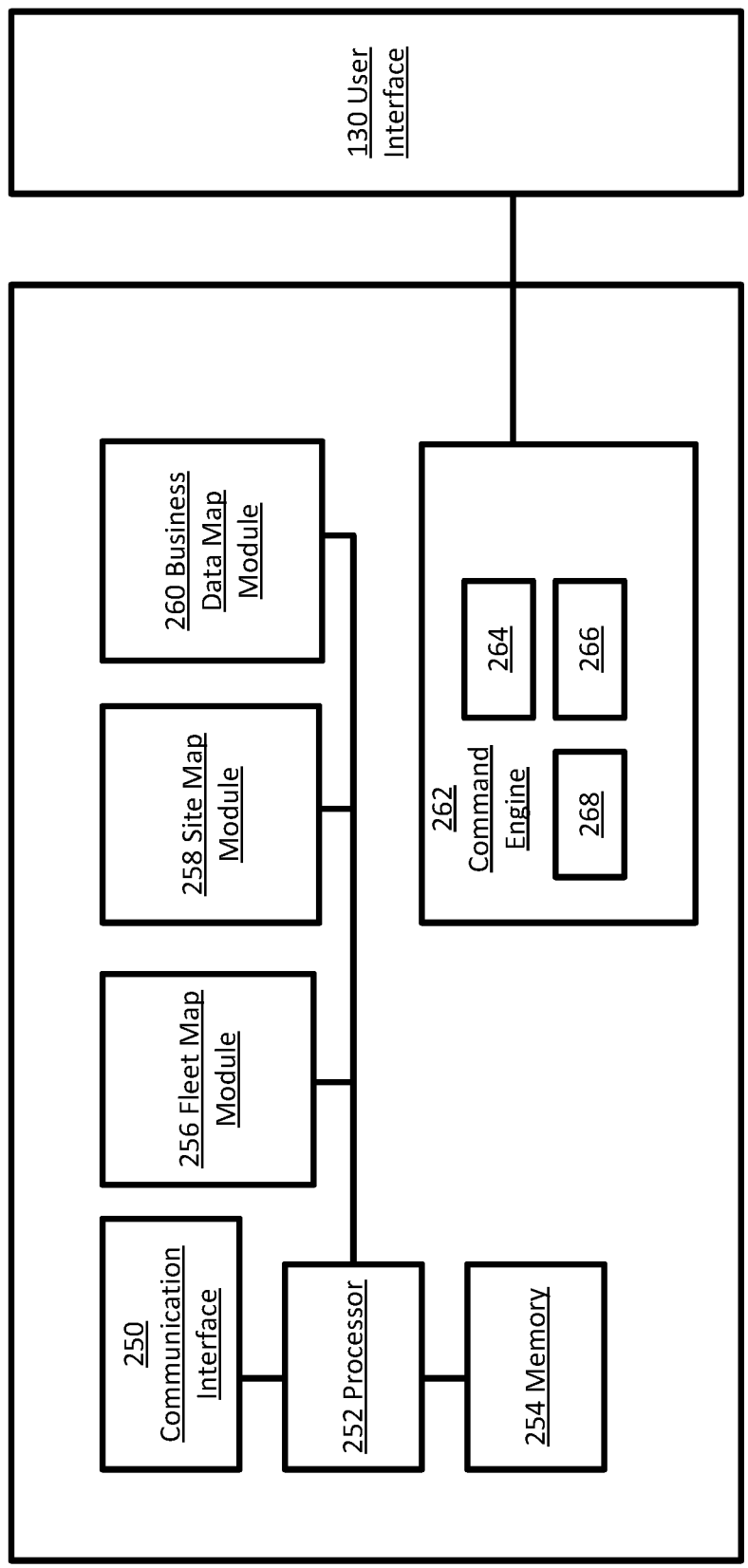
FIG. 2 depicts an example data meta server of the system of FIG. 1.

FIG. 2 depicts an example DM server 120. The DM server 120 includes a processor 252, memory 254, communication interface 250, fleet map module 256, a site map module 258, a business data map module 260, and a command engine 262. The processor 252 is configured to maintain the data meta model. The command engine 262 is configured to receive and interpret requests from the user interface 130. The fleet map module 256, site map module 258, and business data map module 260 are configured to detect changes and update the data meta model. Additional components may be included in the DM server 120. For example, the data repository 110 and user interface 130 may be a part of the DM server 120. The DM server 120 may be in the cloud or on-site at a hospital. The DM server 120 may communicate with the medical devices 105, data repository 110, and a user interface 130 using a network.

The DM server 120 may be configured to receive data from the one or more medical devices 105. The data may be stored in the data repository 110 or in the DM server 120 using an address-based object identifier (path) based on the data source and data attributes. The collection of address based object identifiers may be referred to as the data meta model. The data meta model may describe (map) the location of the source data from a medical device 105 in the datastore. The identifiers may point to map entities. The identifiers may access the map entities in a declarative, logical manner. The identifiers may be used in queries from a business intelligence application or the user interface 130.

The data meta model may include component data maps, such as a fleet map, site map, or business data map.

The identifiers or paths are configurable, updatable, and adaptable. If a new data source or data with different data attributes is identified in the received data, a new address-based object identifier may be generated using the fleet map module 256, site map module 258, and business data map module 260, each of which are configured to track and store separate maps for the fleet, site, and business, respectfully. For example, if the DM server 120 receives a new set of data from a new data source (modality), the new modality may be detected by analyzing the data that the modality had sent. The data may also indicate some properties of the modality (name, type, protocols, etc.). The identifier may be updatable and adaptable based on changes detected or identified by the business, fleet, and/or site modules.

Figure 3:
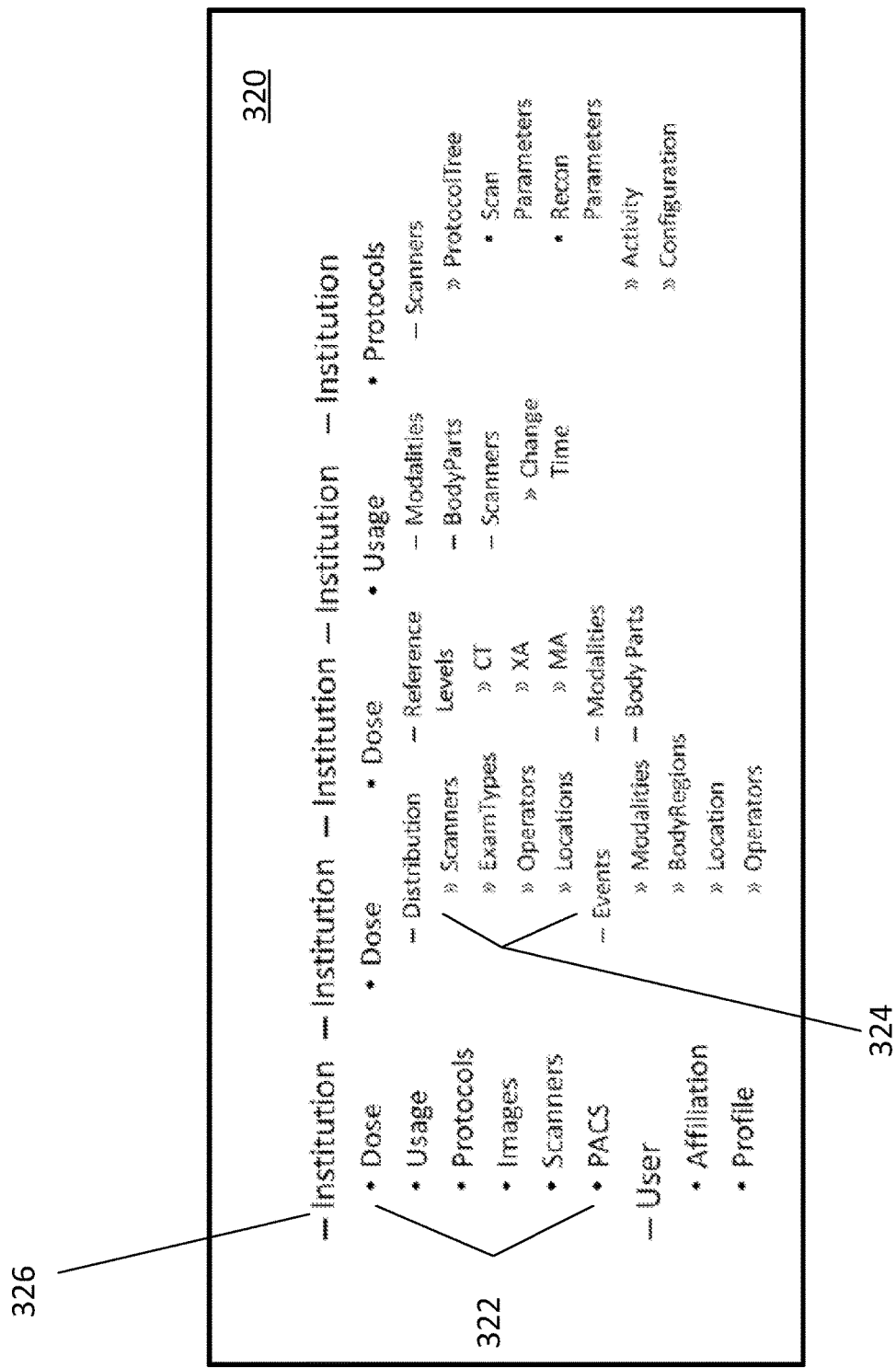
FIG. 3 depicts an example structure of a data meta model.

The data meta model may be configured as a tree structure. FIG. 3 depicts an example tree structure data model 320 for an institution (hospital). The tree structure includes top level categories 326 (institution and user). Each of the top-level categories may have sub-categories 322 (Dose, usage, protocols, images, scanners, PACS). In turn, the sub-categories may have sub sub-categories 324 that may cross references other categories (e.g. the scanners option). The categories in FIG. 3 are just a small sample of categories. Additional, different, or other categories or descriptions may be used.

The data meta model may be configured, updated, adapted, and evolved using the processor 252 based on input from the separate fleet, site, business modules, and from the command engine 262. The processor 252 may include a general processor, digital signal processor, an application specific integrated circuit (ASIC), field programmable gate array (FPGA), analog circuit, digital circuit, combinations thereof, or other now known or later developed processor. The processor 252 may be a single device or combinations of devices, such as associated with a network, distributed processing, or cloud computing. The processor 252 is connected to the memory 254, the communication interface 250, and the map modules.

The memory 254 may be a volatile memory or a non-volatile memory. The memory 254 may include one or more of a read-only memory (ROM), random access memory (RAM), a flash memory, an electronic erasable program read only memory (EEPROM), or other type of memory. The memory 254 may include the data meta model and the data maps. The communication interface 250 may include any operable connection. An operable connection may be one in which signals, physical communications, and/or logical communications may be sent and/or received. An operable connection may include a physical interface, an electrical interface, and/or a data interface. The communication interface 250 provides for wireless and/or wired communications in any now known or later developed format. In one embodiment, the communication interface 250 is a network interface card or cards. The communication interface 250 may be used to communicate with the one or more user interfaces 130. The DM server 120 may be configured in the cloud run as a software as a service model.

Each of the map modules, e.g. the business data map module 260, fleet map module 256, and site map module 258, may be configured to identify and track changes to hospital systems and/or business intelligence applications. The address-based object identifiers in the data meta model may be updated using the fleet map module 256, site map module 258, and or business data map module 260. If, for example, a workflow for a data source changes, the new workflow and subsequent data may be addressed differently. If, for example, a different technician is using the medical device 105, the identifier may be altered. If, for example, a medical device 105 is moved, the identifier may be changed. Alternatively, the identifier may be similar, while relationships in a map or data meta model may be changed. If, for example, a business intelligence application is altered, an identifier may be altered or created. The changes may be tracked and stored so that the map modules may roll back the maps to previous versions. The automatic changes may also searchable even after being implemented in the data meta model.

In an embodiment, the business data map module 260 may maintain a business data map. The business data map module 260 may communicate with the fleet map module 256 and site map module 258 to incorporate input from the fleet map module 256 and site map module 258. The business data map, fleet map, and site map are part of the data meta model and may be updated together. For example, a change in the fleet map may also indicate a change in the business data map. Changes to the data meta model may be made by each of the modules or by a single module.

The business data map module 260 may be configured to update the business data map. The business data map module 260 may be configured to record and describe what the data is and where the data is stored. The business data map module 260 identifies attributes from the data meta model, clinical data, formatted source data (DICOM, HL7, etc.), and PACD or vender neutral archive (VNA) information. The business data map describes what data is and where in the data repository 110 the type of data is. The business data map module 260 identifies the data needs of business intelligence applications. For example, the business data map module 260 may identify that when a business intelligence application requests data for timing, the business data map module 260 may identify data sources that have timing fields. The business data map module 260 may update or adapt identifiers of the data to match the needs of a business intelligence application. The business data map module 260 may communicate with the fleet map module 256 and site map module 258 to identify the one or more medical devices 105 and the hospital environment. The business data map may be automatically generated by the business data map module 260 or may be based on a template data map.

The fleet map module 256 is configured to record and describe the one or more medical devices 105 and the properties of the one or more medical devices 105. The fleet map module 256 may analyze data from the one or more devices such as the administrative data. For example, the fleet map module 256 may analyze data such as the type of scan, the region of the body, and/or patient information (anonymously stored). The fleet map module 256 may be able to identify a type of medical device 105 from the administrative data. The fleet map module 256 may include a library of known devices from different manufacturers. The library may be updated by the manufacturers as new medical devices 105 are implemented. The library may contain possible data attributes for each medical device 105. The fleet map module 256 may be able to determine a workflow or workflows for the medical device 105 from the administrative data. The fleet map module 256 may include a library of used workflows and/or steps. The library may contain previously performed steps for each device, at each hospital, and/or for each user of the medical devices 105. Using the administrative data and exiting or stored objects, the fleet map module 256 may identify fields or attributes for the medical device 105. For example, the fleet map module 256 may identify that data from a medical device 105 relates to an exposure time. The fleet map module 256 may record and store future data from the medical device 105 that is similar as "exposure time" data for the medical device object. The fleet map module 256 may communicate with the business data map module 260 to update the data meta model. For example, a change in a medical device 105 may indicate changes to both the fleet map and the business data map.

The site map module 258 is configured to record a distribution of an organization, e.g. departments, therapy centers, emergency rooms, and the top-level enterprise structure, e.g. all sites and referrers and data centers that are connected. Information identified by the site map component is recorded in a site map. The site map describes how the fleet of medical devices 105 is related to the organization, and thereby provides also basic information about the medical and organizational origin of the acquired data. The site map may be configured initially and updated in a semi-automated manner over time as changes occur. For example, new sites or organizational charts may be manually entered (or automatically if the site map module 258 has access to human resource software or databases). Users for each device may be derived or read automatically from scan data.

The command engine 262 is configured to receive commands from the user interface 130. The command engine 262 may interpret, adjust, and suggest possible solutions or objects for the user interface 130. The command engine 262 includes a medical command interpreter 264, a medical command adaption engine 266, and a medical command suggestion engine 268. Additional components such as a display engine may be included to graphically display the data meta model or maps and command input to a user.

The medical command interpreter 264 may assist in running commands received from the user interface 130. The medical command interpreter 264 may ensure that requests for data from business intelligence applications are interpreted correctly. For example, the medical command interpreter 264 may interpret third-party applications that may use different terminology or structure than the data meta model (e.g. for the level of hospital/institution, protocol management, usage, dose, etc.). New business intelligence applications may be auto-integrated by the medical command interpreter 264 by run-time registration automatically without user input. The medical command interpreter 264 may interpret, adapt, and update requests using the data meta model. The medical command interpreter 264 may allow third party application integration and/or connection, which allows for benchmarks to be run across multiple hospitals and sites. The medical command interpreter 264 may communicate with third party application developers to determine how to interpret terminology or structure in the business intelligence applications. For the user interface 130, the medical command interpreter 264 may analyze the current work context from the user interface 130 and submit entities and components that fit in the context (with help from the medical command suggestion engine).

The medical command adaption engine 266 may help implement any changes to the data meta model. The medical command adaption engine 266 may identify and adapt any changes in the data meta model. The medical command adaption engine 266 may adapt data paths for the user interface 130 and business intelligence applications that use data that has changed. For example, the medical command adaption engine 266 may add or remove a scanner from an existing business intelligence application if the scanner is moved or changed. The medical command adaption engine 266 identifies any changes to the data meta model and makes the appropriate changes to the business intelligence applications that are affected. The medical command adaption engine 266 may update the user interface 130 with any changes to the data meta model.

The medical command suggestion engine 268 analyzes the current work context of the user interfaces 130 and provides an updated set of entities and components that relate to the context. The medical command suggestion engine 268 may correct commands and identifiers. For example, if the user interface 130 has selected a first category, the medical command suggestion engine 268 may suggest related categories or types of data. The medical command suggestion engine 268 may record, store, and analyze business intelligence applications and or the inputs from the user interface 130 to generate relationships.

The DM server 120 may be initially empty. Each of the individual maps (fleet, site, and business) may be created based on a template, for example a similar site or hospital. The data meta model may be derived from each of the individual maps. The data meta model may be populated with a standard or typical set of categories or objects. As each device is detected, the device and the attributes may be identified and added to each of the maps and the data meta model. When devices or data types or format change, the data meta model may be altered to reflect the changes. Alternatively, the DM sever 120 is gradually populated by automatically adapting as each device and/or application is used.

Figure 4:
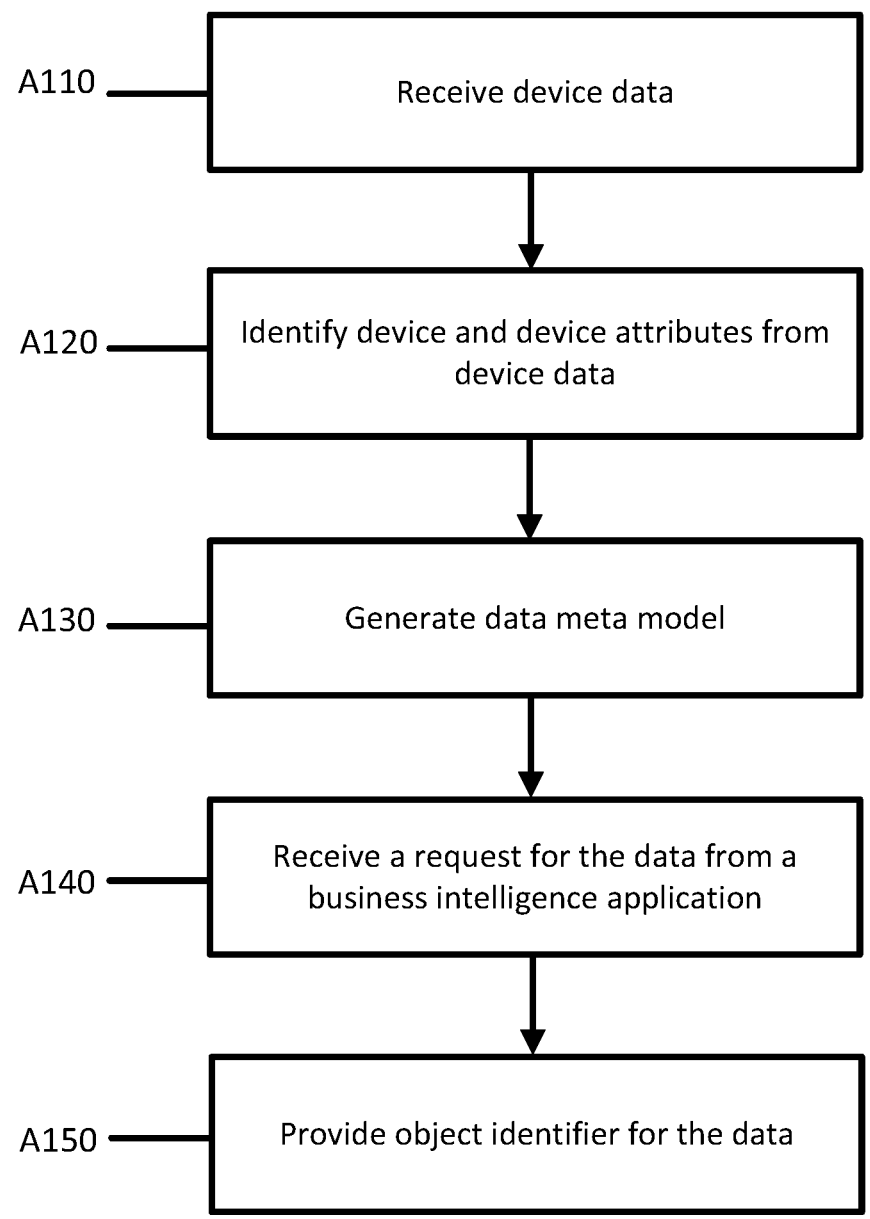
FIG. 4 depicts an example workflow for negotiating between a business intelligence application and one or more data sources.

FIG. 4 depicts an example workflow for negotiating between a business intelligence application and one or more data sources. FIG. 4 represents both populating and using the data meta model. The acts are performed in the order shown, but other orders may be used. Additional, different, or fewer acts may be used, such as performing just acts 110-130 or just acts 140-150.

At act A110, data is received from a plurality of medical devices 105. The medical devices 105 may be medical imaging devices such as a CT, PET, or SPECT scanner. Data from other devices that generate medical or hospital related data may be used. The medical devices 105 may generate source data during operation of the medical devices 105. The source data may be stored in a data repository 110, e.g. a PACS or cloud storage. Data may be continuously received from the one or more medical devices 105. Data also may be stored and batched prior to being received. Data may also be historical data that has previously been stored.

At act A120, a data source and data attributes are identified for the data. The data may include result data (such as image data) and administrative data (such as business data that describes a procedure or workflow that was used to capture the result data). The administrative data may include attributes of the data such as the modality (type of device), the body region, the time of the scan, the technician, etc. The source data may be formatted using a DICOM, HL7, or another standard. DICOM, HL7, and other formatting standards may include administrative data in specific fields that corresponds to attributes of the medical device 105 and underlying results data.

At act A130, a data meta model is generated. The data is mapped to an object identifier based on the data source and data attributes. The data meta model may be stored and updated when changes occur to one or more of the medical devices 105 or the hospital environment. The data meta modal may include one or more component maps, such as a fleet map, a site map, and or a business data map. The data meta model is used to address locations of received data in a data repository 110. The data repository 110 may store the data from the medical devices 105 using an object based architecture. The data from the medical devices 105 may be managed and addressed as objects that include descriptive properties. As changes occur that affect a medical device 105, the object and descriptive properties that represent the medical device 105 may change as well. Changes may be detected by monitoring the incoming data from the medical devices 105. The administrative data (such as business data that describes a procedure or workflow that was used to capture the result data) may indicate that a change has occurred for a medical device 105. The changes may also be made manually by a user. Changes to the site map may be made by monitoring, for example, an organizational chart that details users and responsibilities. When new medical devices 105 are added to the system, a new object may be generated with expected properties. For example, a new object that is similar to existing objects that describe existing CT scanners may be generated for a new CT scanner in the hospital. The new object may be updated as data is received from the new CT scanner.

At act A140, a request for data is received from a business intelligence application. Business intelligence applications may be used to evaluate how a hospital is run. In order to evaluate a hospital or procedure, the business intelligence application needs to analyze relevant data. For example, a business intelligence application that evaluates turnover time for PET scans may require data from each PET scanner, data for the location of each PET scanner, data for each technician that uses the scanner, etc. The business intelligence application may be a third-party application. For example, the business intelligence application may have previously been encoded or used in alternative sites of hospitals. Such an application may have issues accessing the data at a new site. An application that is coded to work at a first site may not be compatible with a second site. A command engine 262 may be used to negotiate, using the data meta model, between the business intelligence application and the one or more medical devices 105 or database 110. The command engine 262 may interpret commands from the business intelligence application and match the commands to objects in the data meta model.

A request may be received from a user interface 130. A script for evaluation may be crafted from scratch or edited using the user interface 130. The user interface 130 may provide objects from the data meta model for selection by a user or application. The user interface 130 may include a graphical representation of the data meta model. The command engine 262 may also assist a user in operating the user interface 130. The command engine 262 may suggest or auto adapt commands inputted by a user to match the objects in the data meta model.

At act A150, the object identifier is provided to the business intelligence application. The business intelligence application may use the object identifier to access the data that the business intelligence application needs to evaluate a hospital or site. The object address may be used as a data path for the business intelligence application to access the requested data.

Business intelligence applications may require data over a period of time. For example, in order to evaluate a workflow, multiple procedures may be performed using the workflow. Alternative workflows may also be measured at the same time to create a baseline for evaluation. The request described above at act A140 may be repeated at predetermined intervals. The data for an object may also be pushed to the business intelligence application as the data is generated by the one or more medical devices 105. Over a period of time, the medical devices 105, workflows, or data may be changed. For example, a business intelligence application may be evaluating the CT scanners at a hospital site. One of the CT scanners may be updated with new software that provides additional or different types of data. One of the CT scanners may be moved to a different location. A workflow for one of the CT scanners may be changed. In each of the scenarios, the data from the CT scanner may be different than when the business intelligence application was implemented. Without adjusting or recoding the business intelligence application, the data meta model may be adjusted to track any changes. The command engine 262 may automatically update any prior interpretations that the command engine 262 had made. The business intelligence application may continue to evaluate the CT scanners with the new data (if the data is relevant) or without the new data (if it is not relevant). Non-relevancy here may be determined if the change to the CT scanner generates data that is no longer useful to the business intelligence application.

Figure 5:
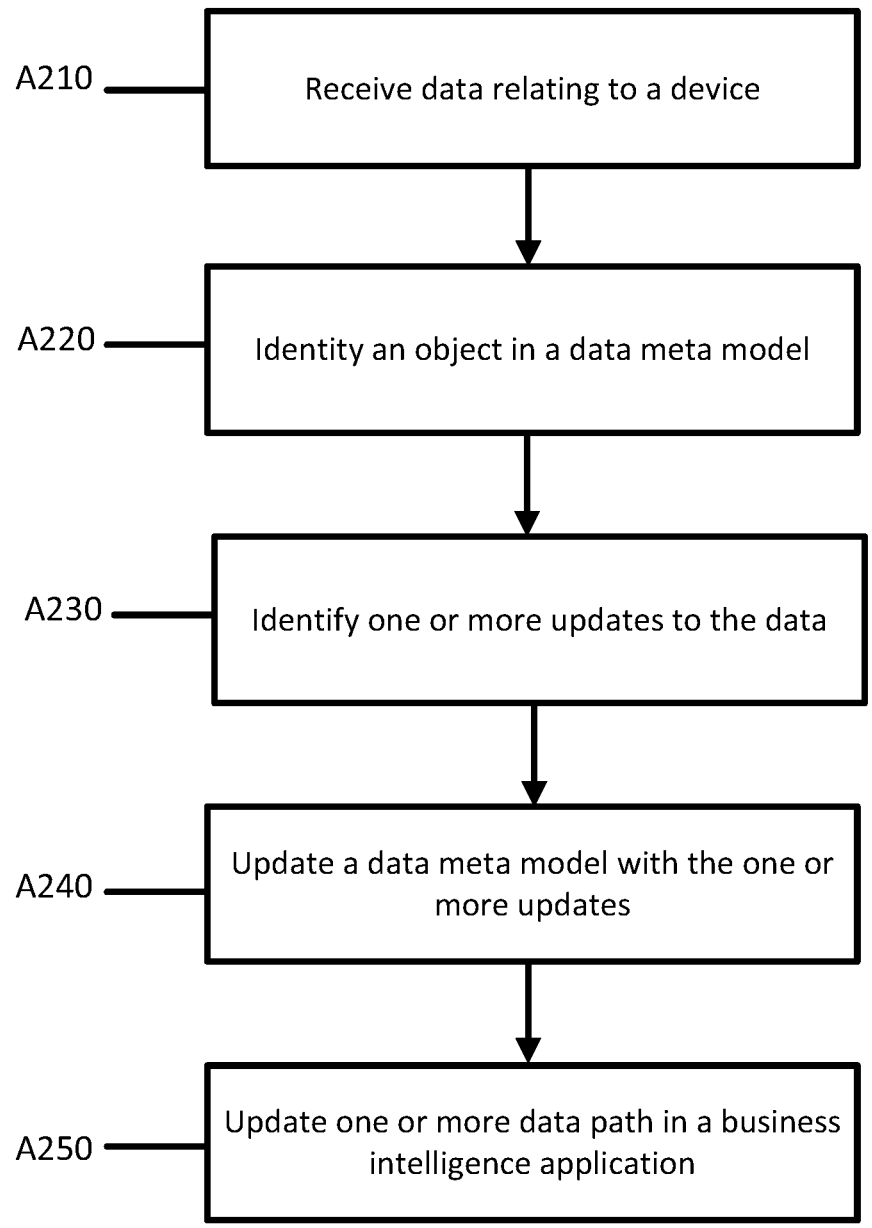
FIG. 5 depicts an example workflow for updating a data meta model for business intelligence applications.

FIG. 5 depicts an example workflow for updating a data meta model for business intelligence applications. As presented in the following sections, the acts may be performed using any combination of the components indicated in FIG. 1 or 2. The following acts may be performed by the user interface 130, the DM server 120, the command engine 262, or a combination thereof. Additional, different, or fewer acts may be provided. For example, prior to act A210, the data may be stored in the data repository 110 or the data may be generated by a medical device 105. The data may be analyzed for changes in act A230 by multiple modules (fleet, site, business data). The acts are performed in the order shown or other orders. The acts may also be repeated.

At act A210, data is received from a medical device 105. The data may include both result data from a procedure (such as image data) and administrative (business) data that describes the procedure. Additional data may be included that relates to the procedure such as notes from a user or patient data. Multiple related procedures may be combined to produce one group of data. The administrative data may include data that describe the procedure such as the region of the scan, the timing, the workflow, the settings of the scanner, etc. The administrative data may further contain data that describes the medical device 105 that acquired the data. The make and model of the medical device 105 or capabilities may be identified from the data.

At act A220, an object in a data meta model is identified that relates to the data. A data meta model may include one or more objects that represent data sources. A medical device 105, for example, may include one or more data sources (e.g. one data source for each body regions, one data source for timing, etc.). The data meta model and the addresses of the objects in the data meta model describe the operation and relationship between the data sources.

At act A230, the data is analyzed for changes. When data is received from a medical device 105, the attributes of the data may be checked against the data meta model to determine if there are any discrepancies or changes. The data meta model may also include component models and/or maps such as a fleet map, site map, or business data map that describe the fleet, site, and data respectively. Changes may be detected by comparing the received data against the data fields and formatting that is expected from each data source.

At act A240, the data meta model is updated with the detected changes. The object identifier may be changed for the data source. For certain changes, only a portion of the object identifier may be changed. For example, a CT scanner that moves from one location to another may have a locational component changed, but not the modality, etc. However, when a business intelligence application requests data from for example, the west wing of a hospital (where the CT scanner used to be), the data provided will no longer include the data for this CT scanner now in the east wing. Changes for the data source or medical device 105 may be recorded in the fleet map, site map, and/or the business data map. Fleet map changes may include: a scanner added, a scanner removed, scanner changes to image types, scanner software updated, and/or scanner name changed. Site map changes may include the scanner changing location, a new site, removing a site, adding, changing, or removing personal, and/or changes in PACS software. Business data map changes may include data moved to another site, data changes in PACS, and/or new data types.

In an embodiment, changes may be made manually by a user to the business data map, the fleet map, and/or the site map. For example, a new user may be added to the site map. The changes may then propagate to the data meta model.

At act A250, data paths for a business intelligence application are updated. Business intelligence applications may be coded to access data in a specific manner. For example, a business intelligence application may be configured to retrieve data from a specific type of medical device 105 using a data path. If a change were to occur to one of the medical devices 105 (e.g. a name change), the business intelligence application may not be able to access the data required to make a correct evaluation. When the change occurs, the data paths may be automatically altered based on the updated data meta model. The business intelligence application may then access the correct data by communicating through the updated data meta model.

Figure 6:
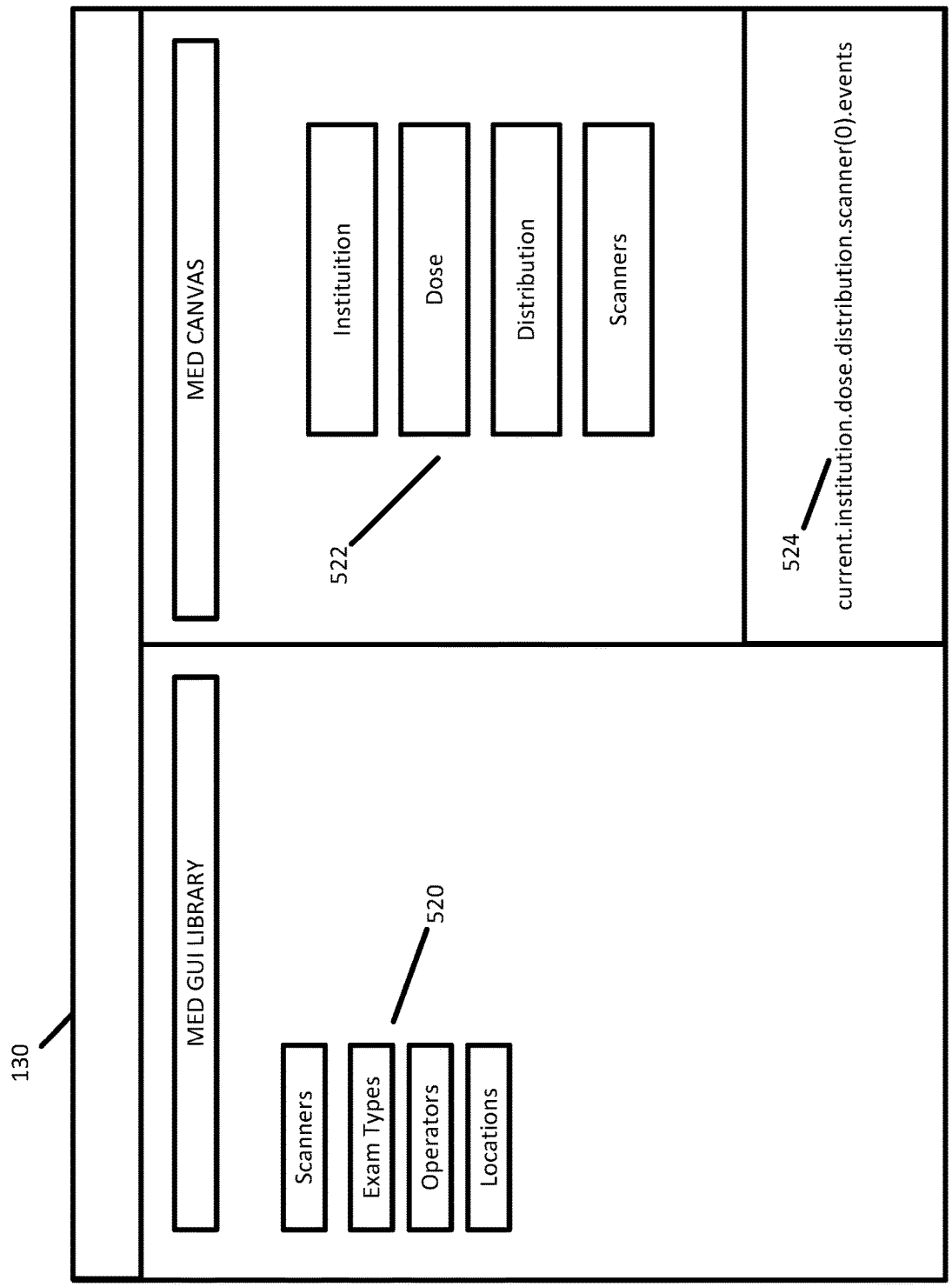
FIG. 6 depicts an example graphical user interface for coding business intelligence applications that use a data meta model for data access in a hospital network.

FIG. 6 depicts an example user interface 130. The user interface 130 in FIG. 6 is a graphical interface that uses boxes and lines to generate evaluations of a hospital (business intelligence applications). As shown in FIG. 6, the user interface 130 includes a medical library 520 from which objects may be selected. The user interface 130 includes a canvas 522 that displays the current selections. As a user selects objects in the medical library, other related objects are displayed for selection. For example, if the user selects the scanner category, the user interface 130 may display all possible scanner types. If the user then selects a CT scanner type, the exam types, operators, and locations may be changed to include only objects that are related to CT scanners. The medical library 520 may only present the choices that make logical sense to the user. For example, if the user selects a body region object, the medical library 520 may not offer as choices scanners that do not scan that body region. A script generator 524 generates a script form the selections in the canvas 522. The script may then be run to evaluate the data in the objects selected.

The illustrations of the embodiments described herein are intended to provide a general understanding of the structure of the various embodiments. The illustrations are not intended to serve as a complete description of all of the elements and features of apparatus and systems that utilize the structures or methods described herein. Many other embodiments may be apparent to those of skill in the art upon reviewing the disclosure. Other embodiments may be utilized and derived from the disclosure, such that structural and logical substitutions and changes may be made without departing from the scope of the disclosure. Additionally, the illustrations are merely representational and may not be drawn to scale. Certain proportions within the illustrations may be exaggerated, while other proportions may be minimized. Accordingly, the disclosure and the figures are to be regarded as illustrative rather than restrictive.

While this specification contains many specifics, these should not be construed as limitations on the scope of the invention or of what may be claimed, but rather as descriptions of features specific to particular embodiments of the invention. Certain features that are described in this specification in the context of separate embodiments may also be implemented in combination in a single embodiment. Conversely, various features that are described in the context of a single embodiment may also be implemented in multiple embodiments separately or in any suitable sub-combination. Moreover, although features may be described above as acting in certain combinations and even initially claimed as such, one or more features from a claimed combination may in some cases be excised from the combination, and the claimed combination may be directed to a sub-combination or variation of a sub-combination.

Similarly, while operations are depicted in the drawings and described herein in a particular order, this should not be understood as requiring that such operations be performed in the particular order shown or in sequential order, or that all illustrated operations be performed, to achieve desirable results. In certain circumstances, multitasking may be advantageous. Moreover, the separation of various system components in the embodiments described above should not be understood as requiring such separation in all embodiments One or more embodiments of the disclosure may be referred to herein, individually and/or collectively, by the term "invention" merely for convenience and without intending to voluntarily limit the scope of this application to any particular invention or inventive concept. Moreover, although specific embodiments have been illustrated and described herein, it should be appreciated that any subsequent arrangement designed to achieve the same or similar purpose may be substituted for the specific embodiments shown. This disclosure is intended to cover any and all subsequent adaptations or variations of various embodiments. Combinations of the above embodiments, and other embodiments not specifically described herein, will be apparent to those of skill in the art upon reviewing the description.

The Abstract of the Disclosure is provided to comply with 37 C.F.R. § 1.72(b) and is submitted with the understanding that it will not be used to interpret or limit the scope or meaning of the claims. In addition, in the foregoing detailed description, various features may be grouped together or described in a single embodiment for the purpose of streamlining the disclosure. This disclosure is not to be interpreted as reflecting an intention that the claimed embodiments require more features than are expressly recited in each claim. Rather, as the following claims reflect, inventive subject matter may be directed to less than all of the features of any of the disclosed embodiments. Thus, the following claims are incorporated into the detailed description provided herein, with each claim standing on its own as defining separately claimed subject matter.

It is therefore intended that the foregoing detailed description be regarded as illustrative rather than limiting, and that it be understood that it is the following claims, including all equivalents, that are intended to define the spirit and scope of this invention.

We claim:

1. A system for integrating one or more business intelligence applications into a hospital network, the system comprising:
one or more medical devices in a hospital configured to generate administrative data that describes a procedure or workflow used to capture result data;
one or more data repositories configured to store the administrative data;
a user interface configured to execute the one or more business intelligence applications using the administrative data; and
a data meta processor configured to generate a data meta model of a plurality of object identifiers that identify a location of stored administrative data for the one or more medical devices, the data meta model including a data structure based on attributes of the administrative data, a fleet map, and a site map of the hospital network, the data meta processor further configured to receive the administrative data from the one or more medical devices, generate an object identifier for the administrative data using the data meta model, and store the administrative data in a data repository of the one or more data repositories using the object identifier;
wherein the data meta processor is further configured to detect a change in the administrative data from previously received administrative data and update the data meta model based on the change in the administrative data;
wherein the data meta processor is further configured to detect a change in the site map of the hospital network and update the data meta model based on the change in the site map;
wherein the user interface is configured to suggest a plurality of object identifiers to match a data request, match the data request from the one or more business intelligence applications to an associated object identifier, and retrieve the administrative data from the data repository using the associated object identifier.

2. The system of claim 1, wherein the one or more medical devices are medical imaging devices.

3. The system of claim 1, wherein the change is detected based on the attributes of the administrative data.

4. The system of claim 1, wherein the data meta processor is further configured to detect a change in the fleet map of the one or more medical devices, wherein the data meta processor is configured to update the data meta model based on the change.

5. A method for integrating one or more business intelligence applications into a hospital network, the method comprising;
receiving, by a data meta processor, business data generated by a plurality of medical devices that describes a procedure or workflow used to capture result data;
identifying, by the data meta processor, a plurality of data sources and a plurality of data attributes for the business data;
generating, by the data meta processor, a data meta model including a fleet map of the plurality of medical devices, a site map of a hospital network, and a plurality of object identifiers that identifies a location of stored business data for the plurality of medical devices, the data meta model including a data structure based on attributes of the business data, a fleet map, and a site map of the hospital network;
generate an object identifier for the business data as a function of the data meta model;
storing, by the data meta processor, the business data in a data repository using the object identifier;
detecting, by the data meta processor, a change in the business data from previously received business data and updating the data meta model based on the change in the business data;
detecting, by the data meta processor a change in the site map of the hospital network and updating the data meta model based on the change in the site map;
receiving, by the data meta processor, a request for the business data from a business intelligence application
suggesting, by the data meta processor, a plurality of object identifiers to match a data request;
matching, by the data meta processor, the data request from the one or more business intelligence applications to an associated object identifier; and
providing, by the data meta processor, the business data from the data repository using the associated object identifier.

6. The method of claim 5, wherein the plurality of data attributes includes a body region scanned by the plurality of medical devices.

7. The method of claim 5, further comprising:
receiving, by the data meta processor, new business data generated from a new medical device;
identifying, by the data meta processor, a new data source and a plurality of new data attributes for the new business data; and
updating, by the data meta processor, the data meta model with the new data source and new data attributes.

8. The method of claim 5, wherein the data meta model comprises the fleet map configured to describe the plurality of medical devices, the site map configured describe a hospital site where the plurality of medical devices are located, and a business data map that describes a plurality of types of business data generated by the plurality of medical devices.

* * * * *